(12) United States Patent
Matsusaki et al.

(10) Patent No.: US 12,326,433 B2
(45) Date of Patent: Jun. 10, 2025

(54) ABNORMAL CARDIAC RHYTHM MYOCARDIAL MODEL AND METHOD FOR PRODUCING SAME, AGENT FOR FORMING ABNORMAL CARDIAC RHYTHM MYOCARDIAL MODEL, AND METHOD FOR EVALUATING DRUG EFFICACY OF HEART DISEASE THERAPEUTIC

(71) Applicants: TOPPAN PRINTING CO., LTD., Tokyo (JP); OSAKA UNIVERSITY, Suita (JP)

(72) Inventors: Michiya Matsusaki, Suita (JP); Shiro Kitano, Tokyo (JP); Shinji Irie, Tokyo (JP)

(73) Assignees: TOPPAN PRINTING CO., LTD., Tokyo (JP); OSAKA UNIVERSITY, Osaka (JP)

( * ) Notice: Subject to any disclaimer, the term of this patent is extended or adjusted under 35 U.S.C. 154(b) by 421 days.

(21) Appl. No.: 16/644,059

(22) PCT Filed: Sep. 3, 2018

(86) PCT No.: PCT/JP2018/032643
§ 371 (c)(1),
(2) Date: Mar. 3, 2020

(87) PCT Pub. No.: WO2019/045105
PCT Pub. Date: Mar. 7, 2019

(65) Prior Publication Data
US 2021/0063374 A1    Mar. 4, 2021

(30) Foreign Application Priority Data
Sep. 4, 2017 (JP) .................................. 2017-169688

(51) Int. Cl.
*G01N 33/15* (2006.01)
*C07K 14/78* (2006.01)
*C12N 5/077* (2010.01)

(52) U.S. Cl.
CPC ............. *G01N 33/15* (2013.01); *C07K 14/78* (2013.01); *C12N 5/0657* (2013.01)

(58) Field of Classification Search
CPC .................................................. A61K 38/014
See application file for complete search history.

(56) References Cited

U.S. PATENT DOCUMENTS

2015/0202348 A1*  7/2015  Dvir ................. A61L 27/52
                                                       424/572
2017/0173215 A1*  6/2017  Tung ................ A61L 27/3808

FOREIGN PATENT DOCUMENTS

| JP | 2017-15958 | 1/2017 |
|---|---|---|
| WO | WO 01/09319 A1 | 2/2001 |
| WO | WO 01/83705 A1 | 11/2001 |
| WO | WO 2015/025957 A1 | 2/2015 |
| WO | WO-2015081226 A1 * | 6/2015 ......... A61L 27/3683 |

OTHER PUBLICATIONS

Lee et al. (Jul. 2017) Contractile force generation by 3D hiPSC-derived cardiac tissues is enhanced by rapid establishment of cellular interconnection in matrix with muscle-mimicking stiffness, Biomaterials, vol. 131, pp. 111-120.*
Eschenhagen T et al. Three-dimensional reconstitution of embryonic cardiomycetes in a collagen matrix: a new heart muscle model system. FASEB J. 1997. 11, 683-694. (Year: 1997).*
Chung L et al. Collagenase unwinds triple helical collagen prior to peptide bond hydrolysis. 2004. The EMBO Journal. 23. 3020-3030. (Year: 2004).*
Japanese Office Action dated Jan. 4, 2023 in Japanese Patent Application No. 2019-539708 (9 pages).
Yuto Amano et al., "Development of vascularized iPSC derived 3D-cardiomyocyte tissues by filtration Layer-by-Layer technique and their application for pharmaceutical assays"; Acta Biomaterialia 33 (2016) 110-121; (19 pages).
Ayami Hiura et al., "Construction of cardiac tissue made from iPS-derived cardiomyocytes by coating cell surfaces with collagen and introduction of blood vessel structure", May 10, 2016, vol. 65, No. 1, p1Ph120; (5 pages).
Koki Nishi et al., "Construction of iPS cell-derived cardiomyocytic tissue using collagen microfiber", May 15, 2017, vol. 66, No. 1, p2Pa097; (4 pages).
Office Action mailed Sep. 20, 2022 in Japanese Patent Application No. 2019-539708 (5 pages).
Office Action dated Jan. 18, 2023 in Japanese Patent Application No. 201880056761.5 (14 pages).
Guo et al, "Three-Dimensional Geometry of Honeycomb Collagen Promotes Higher Beating Rate of Myocardial Cells in Culture", *Artificial Organs*, Apr. 2012, vol. 36, p. 816-819++.
Van Spreeuwel et al., "Mimicking Cardiac Fibrosis in a Dish: Fibroblast Density Rather than Collagen Density Weakens Cardiomyocyte Function", *Journal of Cardiovascular Translational Research*, Apr. 2017, vol. 10, p. 116-127++.
International Search Report dated Dec. 4, 2018, in corresponding International Patent Application No. PCT/JP2018/032643 (2 pages).
Amano et al., "Development of vascularized iPSC derived 3D-cardiomyocyte tissues by filtration Layer-by-Layer technique and their application for pharmaceutical assays", *Acta Biomaterialia*, Jan. 2016, vol. 33, p. 110-121**.
Hiura et al., "Construction of cardiac muscular tissue composed of iPS-derived cardiomyocyte obtained by coating cell surface with collagen, and introduction of blood vessel-like structure", *Polymer preprints*, Japan, May 2016, vol. 65, No. 1 (4 pages)**.

(Continued)

*Primary Examiner* — Paul J Holland
(74) *Attorney, Agent, or Firm* — STAAS & HALSEY LLP

(57) ABSTRACT

The present invention relates to an abnormal cardiac rhythm myocardial model composed of a three-dimensional tissue containing cells including the cardiomyocytes and collagen, wherein at least a portion of the cells adheres to the collagen.

20 Claims, 12 Drawing Sheets

(56) References Cited

OTHER PUBLICATIONS

Nishi et al., "Construction of iPS cell-derived cardiomyocyte tissue using collagen microfiber", *Polymer preprints*, Japan, May 2017, vol. 66, No. 1 (5 pages)**.

Nishi et al., "Establishment of iPS cell-derived cardiac fibrosis model using collagen microfiber", *Polymer preprints*, Japan, Sep. 2017, vol. 66, No. 2 (7 pages)**.

Nishi et al., "Establishment of human iPS cell-derived cardiac fibrosis model using collagen microfiber and control of cardiac fibrosis", *Polymer preprints*, Japan, May 2018, vol. 67, No. 1 (5 pages)**.

Zuppinger Christian et al., "3D culture for cardiac cells", *Biochimica et Biophysica Acta* vol. 1863, No. 7, Dec. 2, 2015, pp. 1873-1881**.

T. Kofdis et al., "In vitro engineering of heart muscle: Artificial myocardial tissue", *The Journal of Thoracic and Cardiovascular Surgery*, vol. 124, No. 1, Jul. 1, 2002, pp. 63-69**.

Kawatou Masahide et al., "Modelling Torsiarde de Pointes arrhythmias in vitro in 3D human iPS cell-engineered heart tissue", *Nature Communications*, vol. 8, No. 1, Oct. 20, 2017, pp. 1-11**.

Veldhuizen Jaimeson et al., "Three-dimensional microengineered models of human cardiac diseases", *Journal of Biological Engineering*, vol. 13, No. 1, Apr. 3, 2019, pp. 1-12**.

Extended European Search Report dated Mar. 15, 2021, in corresponding European Patent Application No. 18850760.2.

\* cited by examiner

Fig. 3(A)
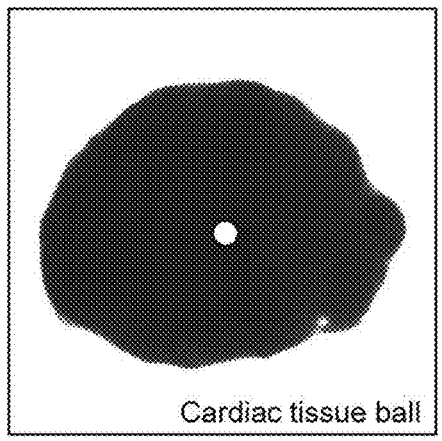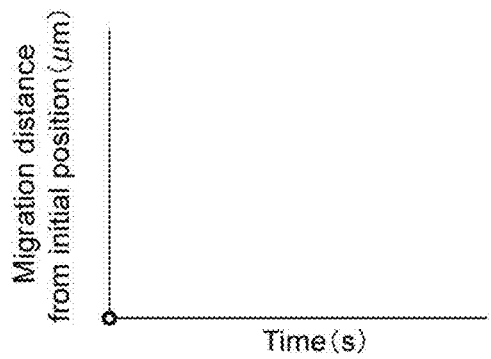
Cardiac tissue ball
○ Initial position of center of gravity
Fig. 3(B)
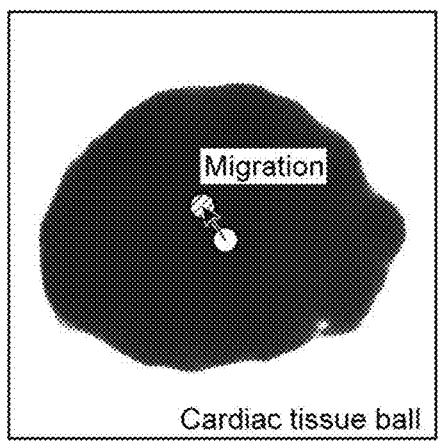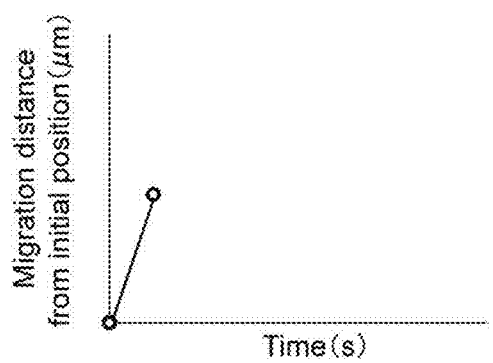
Cardiac tissue ball
○ Initial position of center of gravity
⊘ New position of center of gravity
Fig. 3(C)
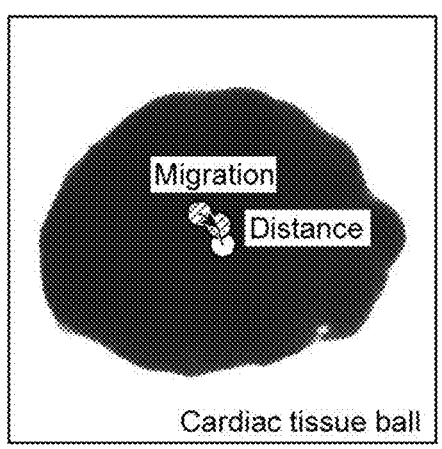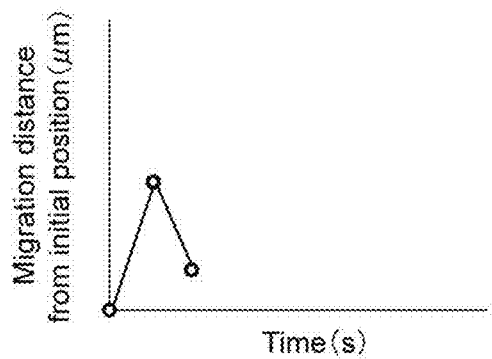
Cardiac tissue ball
○ Initial position of center of gravity
⊘ New position of center of gravity

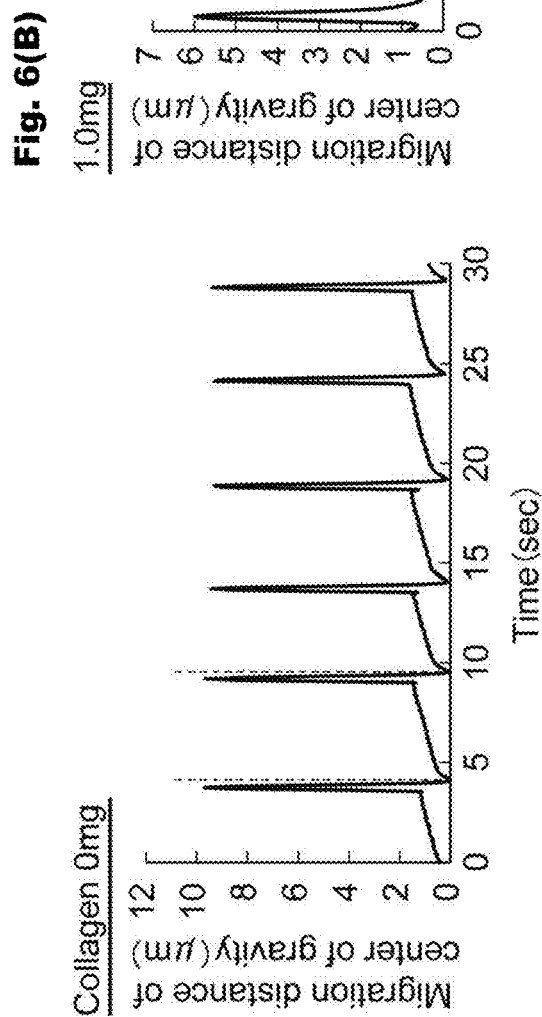
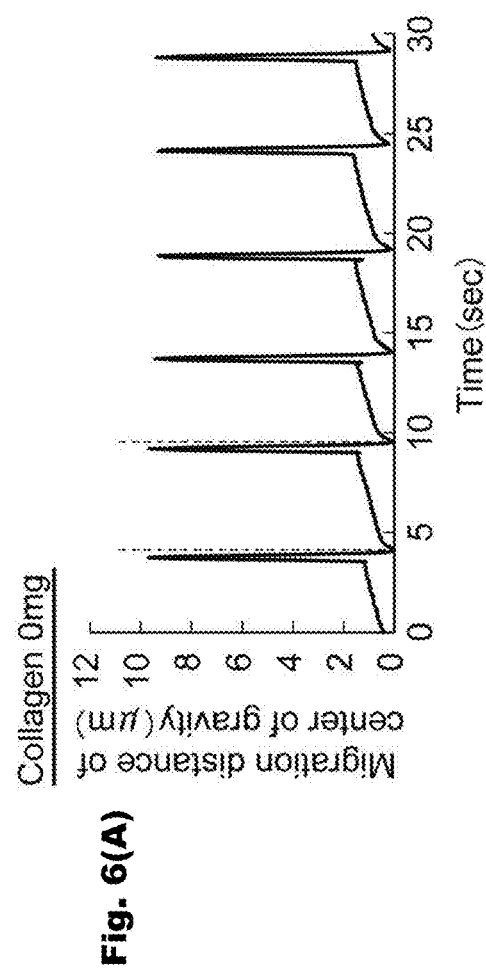
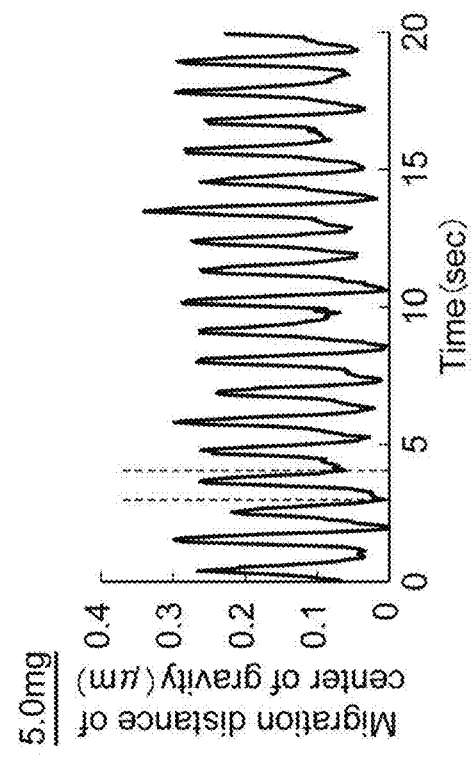
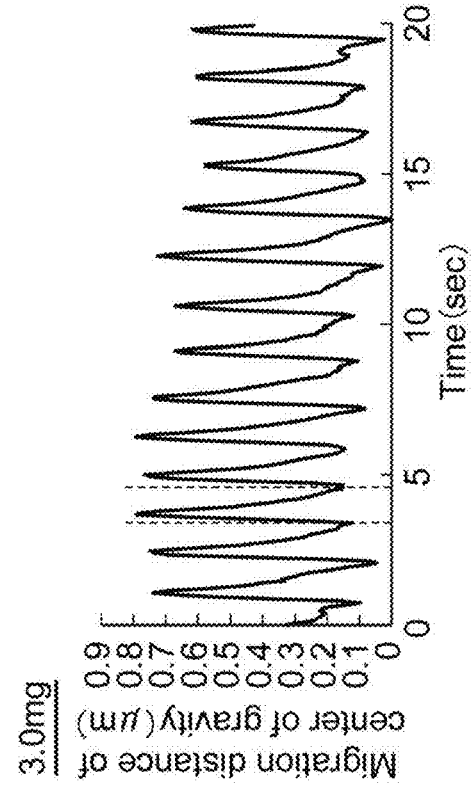
Fig. 6(A) Collagen 0mg
Fig. 6(B) 1.0mg
Fig. 6(C) 3.0mg
Fig. 6(D) 5.0mg

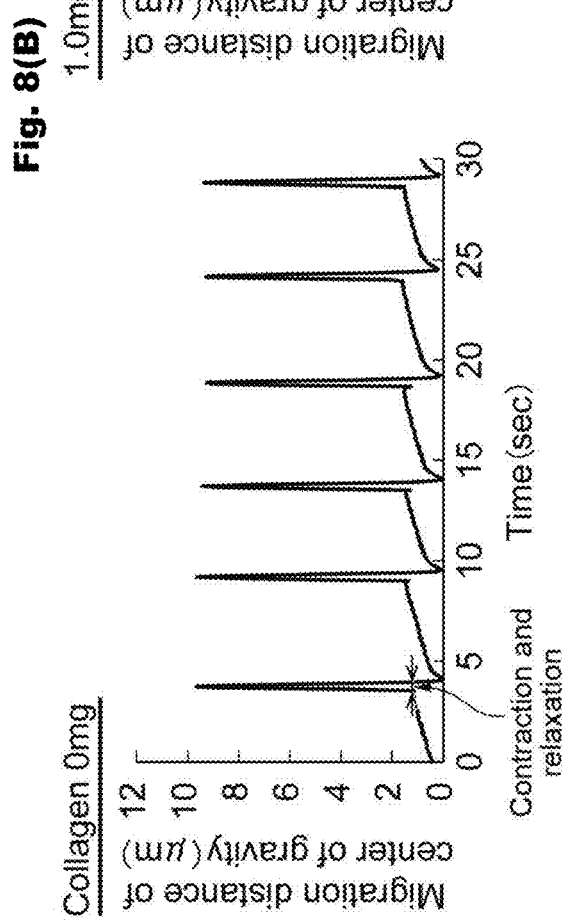
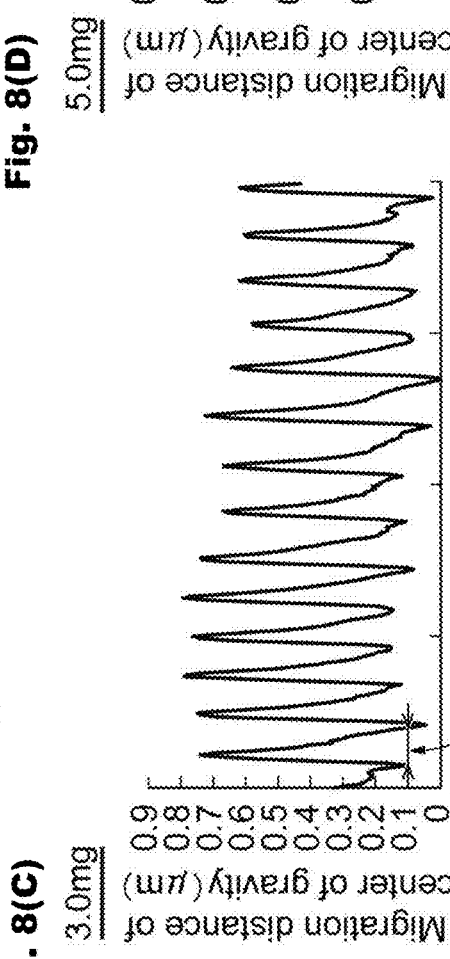
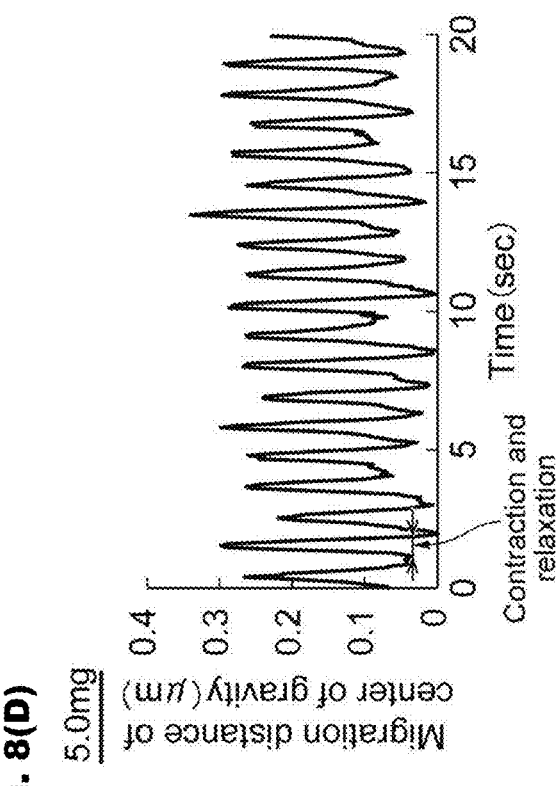
Fig. 8(A) Fig. 8(B) Fig. 8(C) Fig. 8(D)

ABNORMAL CARDIAC RHYTHM MYOCARDIAL MODEL AND METHOD FOR PRODUCING SAME, AGENT FOR FORMING ABNORMAL CARDIAC RHYTHM MYOCARDIAL MODEL, AND METHOD FOR EVALUATING DRUG EFFICACY OF HEART DISEASE THERAPEUTIC

CROSS-REFERENCE TO RELATED APPLICATIONS

This application is a U.S. National Stage Application which claims the benefit under 35 U.S.C. § 371 of International Patent Application No. PCT/JP2018/032643 filed on Sep. 3, 2018, which claims foreign priority benefit under 35 U.S.C. § 119 of Japanese Patent Application No. 2017-169688 filed on Sep. 4, 2017 in the Japanese Intellectual Property Office, the contents of both of which are incorporated herein by reference.

TECHNICAL FIELD

The present invention relates to an abnormal cardiac rhythm myocardial model and a method for producing the same, a formation agent for an abnormal cardiac rhythm myocardial model, and a method for evaluating the drug efficacy of a heart disease therapeutic.

BACKGROUND ART

Recently, techniques for ex vivo construction of cell-based three-dimensional tissues have been developed. Such three-dimensional tissues can be used in biological tissue models and the like available as a substitute for experimental animals Patent Literatures 1 and 2 disclose three-dimensional tissues of cardiomyocytes produced using collagen as a scaffold.

CITATION LIST

Patent Literature

Patent Literature 1: Artif Organs, 2012, Vol. 36, No. 9, pp. 816-819
Patent Literature 2: J. of Cardiovasc. Trans. Res., 2017, 10, pp. 116-127

SUMMARY OF INVENTION

Problems to be Solved by the Invention

The purpose of the present invention is to provide a novel abnormal cardiac rhythm myocardial model and a method for producing the same, and a formation agent capable of being used for production of the abnormal cardiac rhythm myocardial model.

Means for Solving the Problems

The present inventors have conducted intensive research, and as a result, have found that the above problem can be solved by the following items of the present invention.
[1] An abnormal cardiac rhythm myocardial model composed of a three-dimensional tissue containing cells including cardiomyocytes and collagen, wherein at least a portion of the cells adheres to the collagen.
[2] The abnormal cardiac rhythm myocardial model according to [1], wherein the cells further contain a collagen-producing cell.
[3] The abnormal cardiac rhythm myocardial model according to [1] or [2], wherein the content of the collagen is 10 wt % to 30 wt % based on the three-dimensional tissue.
[4] The abnormal cardiac rhythm myocardial model according to any one of [1] to [3], wherein the collagen comprises exogenous collagen.
[5] The abnormal cardiac rhythm myocardial model according to any one of [1] to [4], wherein the collagen comprises fragmented collagen derived from the exogenous collagen.
[6] A method for producing an abnormal cardiac rhythm myocardial model, comprising:
a contact step of bringing the cells including the cardiomyocytes into contact with the exogenous collagen in an aqueous medium; and
a culturing step of culturing the cells in contact with the exogenous collagen,
wherein the amount of the exogenous collagen to be used in the contact step is 0.1 mg or more relative to $1.0 \times 10^5$ to $10.0 \times 10^5$ cells.
[7] The method for producing an abnormal cardiac rhythm myocardial model according to [6], wherein the cells further comprise a collagen-producing cell.
[8] The method according to [7], wherein fragmented collagen is contained as the exogenous collagen.
[9] The method according to [8], wherein an average length of the fragmented collagen is from 100 nm to 200 μm.
[10] The method according to [8] or [9], wherein an average diameter of the fragmented collagen is from 50 nm to 30 μm.
[11] The method according to any one of [6] to [10], further comprising a step of precipitating the exogenous collagen and the cells in the aqueous medium during the contact step or the culturing step.
[12] The method according to any one of [6] to [11], wherein the mass ratio between the exogenous collagen and the cells is 900:1 to 9:1.
[13] A formation agent for an abnormal cardiac rhythm myocardial model, comprising fragmented collagen, wherein an average length of the fragmented collagen is from 100 nm to 200 μm, and an average diameter of the fragmented collagen is from 50 nm to 30 μm.
[14] A method for evaluating drug efficacy of a heart disease therapeutic using the abnormal cardiac rhythm myocardial model according to any one of [1] to [5], comprising: an administration step of administrating a heart disease therapeutic to an abnormal cardiac rhythm myocardial model; and an evaluation step of evaluating the drug efficacy by a change in behavior of the cardiac rhythm of the abnormal cardiac rhythm myocardial model to which the heart disease therapeutic is administrated.
[15] The method for evaluating drug efficacy of a heart disease therapeutic according to [14], wherein in the evaluation step, the heart disease therapeutic is evaluated as effective as a cardiac disorder therapeutic if the number of beats per unit time of the abnormal cardiac rhythm myocardial model to which the heart disease therapeutic is administrated is larger than that of an abnormal cardiac rhythm myocardial model to which the heart disease therapeutic is not administrated, and the heart disease therapeutic is evaluated as not effective as the cardiac disorder therapeutic if the number of beats per unit time of the abnormal cardiac rhythm myocardial model to which the heart disease therapeutic is administrated is smaller than that of an abnormal cardiac rhythm myocardial model to which the heart disease therapeutic is not administrated.

[16] The method for evaluating drug efficacy of a heart disease therapeutic according to [14] or [15], wherein the evaluation step is performed several times.

Effects of the Invention

According to the present invention, a novel abnormal cardiac rhythm myocardial model and the method for producing the same, and a formation agent capable of being used for production of the abnormal cardiac rhythm myocardial model can be provided.

BRIEF DESCRIPTION OF DRAWINGS

FIGS. 3(A)-3(C) are images and graphs for illustrating the method for evaluating the myocardial model.

FIGS. 6(A)-6(D) are graphs showing the results of evaluation of the cardiac rhythm behaviors of the myocardial models.

FIGS. 8(A)-8(D) are graphs showing the results of evaluation of the cardiac rhythm behaviors of the myocardial models.

EMBODIMENTS FOR CARRYING OUT THE INVENTION

Figure 1A:
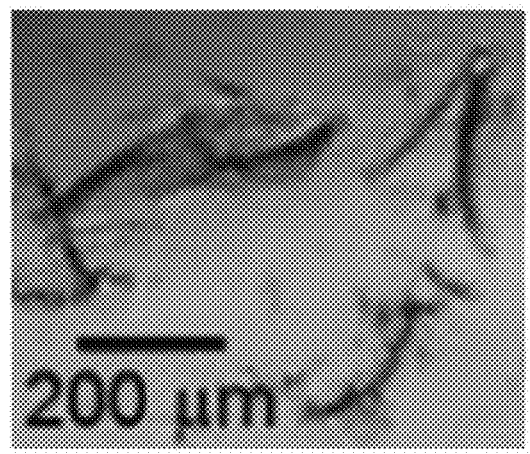
FIG. 1(A) is an image showing fragmented collagens obtained by homogenization for 2 min.

Hereinafter, embodiments will be described in detail. It should be noted that the present invention is not limited to the embodiments below.

Abnormal Cardiac Rhythm Myocardial Model

The abnormal cardiac rhythm myocardial model according to the present embodiment is composed of a three-dimensional tissue containing cells including cardiomyocytes (hereinafter, simply referred to as "cells" in some cases) and collagen, wherein at least a portion of the cells adheres to the collagen.

The "abnormal cardiac rhythm myocardial model" refers to a myocardial model composed of a three-dimensional tissue comprising cardiomyocytes and having a behavior of the cardiac rhythm which is abnormal compared to a normal myocardial model. Examples of the behavior of the cardiac rhythm include the beating interval, the number of beats, the force of cardiac rhythm, and the contraction and/or relaxation rate. The abnormal cardiac rhythm myocardial model may be those whose behaviors of the cardiac rhythm irregularly change, or may be those having a cardiac rhythm increased or suppressed compared to the normal myocardial model. The abnormal cardiac rhythm myocardial model can be used as a heart disease model attributed to an abnormal cardiac rhythm of cardiac muscles (such as a cardiac failure model, an arrhythmia model, or a myocardial infarction model).

Here, the "three-dimensional tissue" means a cell aggregate in which cells are three-dimensionally arranged via collagen such as fibrillar collagen, the cell aggregate being artificially made by cell culturing. Examples of the shape of the three-dimensional tissue include, but are not particularly limited to, a sheet shapes, a spherical shape, an elliptical shape, and a rectangular parallelepiped shape. Examples of a biological tissue include blood vessels, and the structures of these biological tissues are more complex than the structure of a three-dimensional tissue. This makes it possible to easily distinguish between the three-dimensional tissue and a biological tissue.

The three-dimensional tissue contains cells including cardiomyocytes. Examples of original animal species in the cardiomyocytes include a human, a pig, a cow, and a mouse. For example, the cardiomyocytes may be human iPS cell-derived cardiomyocytes (iPS-CM), mouse iPS-derived cardiomyocytes, or ES cell-derived cardiomyocytes. The human iPS cell-derived cardiomyocytes available from, for example, RIKEN Cell Bank or Takara Bio, Inc. can be used. Moreover, because an initializing reagent can be purchased from REPROCELL or the like, iPS cells may be produced in laboratories.

The content of the cardiomyocytes may be 5 to 95% by mass or 25% to 75% by mass based on the three-dimensional tissue.

The cells including the cardiomyocytes may further comprise a collagen-producing cell. In other words, the three-dimensional tissue may comprise endogenous collagen.

Here, the "collagen-producing cell" means a cell which secretes collagen such as fibrillar collagen. Examples of original animal species for the collagen-producing cell include a human, a pig, a cow, and a mouse; and examples of the collagen-producing cell include mesenchymal cells such as fibroblasts (such as human dermal fibroblasts (NHDFs), human cardiac fibroblasts (NHCFs), and human myofibroblasts), chondrocytes, and osteoblasts, and preferred are fibroblasts. Examples of the preferred fibroblasts include human cardiac fibroblasts (NHCFs) or human myofibroblasts.

The "endogenous collagen" means collagen produced by the collagen-producing cell. The endogenous collagen may be fibrillar collagen, or may be non-fibrillar collagen.

The three-dimensional tissue contains the collagen. Examples of the collagen include fibrillar collagens or non-fibrillar collagens. The fibrillar collagen means collagen that is the main component of collagen fibers, and specifically examples thereof include type I collagen, type II collagen, and type III collagen. Examples of the non-fibrillar collagen include type IV collagen.

In the three-dimensional tissue, at least a portion of the cells including the cardiomyocytes adheres to the collagen.

The collagen contained in the three-dimensional tissue may comprise exogenous collagen. The collagen preferably comprises fragmented collagens derived from the exogenous collagen.

The "exogenous collagen" means collagen that is externally supplied, and specifically, examples thereof include fibrillar collagens and non-fibrillar collagens. In the exogenous collagen, original animal species may be the same as those for the endogenous collagen, or may be different therefrom. Examples of the original animal species in the exogenous collagen include a human, a pig, and a cow. The exogenous collagen may also be an artificial collagen. It is preferred that the exogenous collagen be fibrillar collagen. Examples of the fibrillar collagen include type I collagen, type II collagen, and type III collagen, and preferred is type I collagen. For the fibrillar collagen, a commercially available collagen may be used, and specific examples thereof include lyophilized, pig skin-derived type I collagen manufactured by NH Foods Ltd. Examples of non-fibrillar exogenous collagen include type IV collagen.

An original animal species of the exogenous collagen may be different from that of the cardiomyocytes and the cells including the cardiomyocytes. If the cells including the cardiomyocytes comprise the collagen-producing cell, the original animal species for the exogenous collagen may be different from that of the collagen-producing cell. In other words, the exogenous collagen may be heterogeneous collagen.

The "fragmented collagen" means those obtained by fragmenting collagen, such as fibrillar collagen, and having a triple helix structure. One type of collagen may be used alone to make fragmented collagen or a plurality of the types of collagen may be used in combination. Conventionally, collagen such as fibrillar collagen was dissolved in an acidic aqueous solution, etc. However, the concentration thereof was at most about 0.1 to 0.3 wt % so that a large portion was insoluble. Accordingly, it has been difficult that conventional methods are used to increase the amount of collagen, such as fibrillar collagen, in the three-dimensional tissue. It is postulated that fragmented collagen is hardly soluble in water, but when dispersed in aqueous medium, the fragmented collagen is more easily brought into contact with the cells in the aqueous medium, thereby promoting the formation of a three-dimensional tissue.

The average length of the fragmented collagens is preferably from 100 nm to 200 μm, more preferably from 22 μm to 200 μm, and still more preferably from 100 μm to 200 μm. The average diameter of the fragmented collagens is preferably from 50 nm to 30 μm, more preferably from 4 μm to 30 μm, and still more preferably from 20 μm to 30 μm.

A process for making collagen, such as fibrillar collagen, fragmented is not particularly limited. For instance, collagen such as fibrillar collagen may be fragmented by using a homogenizer such as an ultrasonic homogenizer, a stirring homogenizer, and a high-pressure homogenizer. When the stirring homogenizer is used, collagen such as fibrillar collagen may be subject to homogenization as it is or may be subject to homogenization in an aqueous medium such as saline. In addition, it is possible to prepare fragmented collagen at a millimeter or nanometer size by adjusting the time and cycle of the homogenization.

The diameter and the length of the fragmented collagen can be determined by analyzing individual fragmented collagens by using an electron microscope.

The content of the collagen in the three-dimensional tissue may be 0.01 to 90 wt % based on the three-dimensional tissue, preferably 10 to 90 wt %, more preferably 1 to 50 wt %, still more preferably 10 to 40 wt %, and may be 10 to 30 wt %. Here, the term "collagen in the three-dimensional tissue" means collagen constituting the three-dimensional tissue, and may be endogenous collagen or may be exogenous collagen. Namely, the concentration of the collagen constituting the three-dimensional tissue means the total concentration of the endogenous collagen and the exogenous collagen. The concentration of the collagen in the three-dimensional tissue can be calculated from the volume of the resulting three-dimensional tissue and the mass of the decellularized three-dimensional tissue. Moreover, the content of the collagen in the three-dimensional tissue can also be measured by a method using an antigen antibody reaction, such as ELISA, or a chemical detection method, such as QuickZyme.

The residual percentage of the three-dimensional tissue after trypsin treatment at a trypsin concentration of 0.25%, a temperature of 37° C. and a pH of 7.4 for a reaction time of 15 min is preferably 70% or higher, more preferably 80% or higher, still more preferably 90% or higher. Such a three-dimensional tissue is not susceptible to enzymatic degradation during or after culturing and is thus stable. The residual percentage may be calculated from the mass of the three-dimensional tissue before and after the trypsin treatment.

The residual percentage of the three-dimensional tissue after collagenase treatment at a collagenase concentration of 0.25%, a temperature of 37° C., and a pH of 7.4 for a reaction time of 15 min is preferably 70% or higher, more preferably 80% or higher, still more preferably 90% or higher. Such a three-dimensional tissue is not susceptible to enzymatic degradation during or after culturing and is thus stable.

The thickness of the three-dimensional tissue is preferably 10 μm or longer, more preferably 100 μm or longer, still more preferably 1000 μm or longer. Such a three-dimensional tissue has a structure closer to the structure of a biological tissue and is suitable as a substitution for experimental animals. The upper limit of the thickness is not particularly limited and may be, for instance, 10 mm or less, 3 mm or less, 2 mm or less, 1.5 mm or less, or 1 mm or less.

As used herein, the "thickness of a three-dimensional tissue" means the distance between both ends in a direction vertical to the main surface when the three-dimensional tissue has a sheet shape or a rectangular parallelepiped shape. If the main surface has a recess and/or a protrusion, the thickness means the distance across the thinnest portion of the main surface.

When the three-dimensional tissue is spherical, the thickness means the diameter. Furthermore, when the three-dimensional tissue is elliptical, the thickness means the short diameter. If the three-dimensional tissue is substantially spherical or substantially elliptical with a recess and/or a protrusion on the surface, the thickness means the shortest distance between two points at which the surface intersects with a line crossing the center of gravity of the three-dimensional tissue.

Cells constituting the three-dimensional tissue may further contain one or more additional cells other than the cardiomyocytes and the collagen-producing cell.

The three-dimensional tissue may further contain the cells including the cardiomyocytes, and components other than the collagen (additional components). Examples of the additional components include elastin, collagen, proteoglycan, fibronectin, and laminin.

The abnormal cardiac rhythm myocardial model composed of the three-dimensional tissue can be used as a substitute for experimental animals (such as a heart disease model attributed to the abnormal cardiac rhythm of cardiac muscles), a myocardial infarction model, a myocardial fibrosis model, and the like.

Method for Producing Abnormal Cardiac Rhythm Myocardial Model

The method for producing an abnormal cardiac rhythm myocardial model according to the present embodiment comprises a contact step of bringing cells including the cardiomyocytes (hereinafter, simply referred to as "cell" in some cases) into contact with exogenous collagen in an aqueous medium; and a culturing step of culturing the cells brought into contact with the exogenous collagen, wherein the amount of the exogenous collagen to be used in the contact step is 0.1 mg or more relative to $1.0 \times 10^5$ to $10.0 \times 10^5$ cells.

The "aqueous medium" means a liquid comprising water as an indispensable component. The aqueous medium is not particularly limited as long as the exogenous collagen and the cells can be present stably. Examples include saline such as phosphate buffered saline (PBS) and liquid media such as Dulbecco's Modified Eagle medium (DMEM) and vascular endothelial cell-specific medium (EGM2). The liquid medium may be a mixed medium prepared by mixing two different media. It is preferable that the aqueous medium be a liquid medium in view of reducing a load on cells.

Contact Step

The method of bringing the cells including the cardiomyocytes into contact with the exogenous collagen in the aqueous medium is not particularly limited. Examples include: a process involving adding a dispersion of the exogenous collagen to a culture solution containing cardiomyocytes, a process involving adding cells to a culture medium dispersion of the exogenous collagen, and a process involving adding exogenous collagen and cardiomyocytes to a prepared aqueous medium.

In the contact step, the cells may further comprise a collagen-producing cell. In this case, the resulting three-dimensional tissue is more stable, and the cells are more uniformly distributed. The details of the mechanism for producing such a three-dimensional tissue are unclear but are postulated as follows. First, cells are in contact with the exogenous collagen and adhere thereon. Next, the cells, by themselves, produce proteins (e.g., collagen such as fibrillar collagen) constituting an extracellular matrix (ECM). The proteins produced are in contact with the exogenous collagens and adhere thereon, so that the proteins each serves as a cross-linker between the exogenous collagens. In this way, the fibrillar collagen, etc., is structured under an environment where the cells are uniformly present. This results in a stable three-dimensional tissue in which the cells are uniformly distributed. The above postulation does not restrict the present invention.

In the contact step, fragmented collagens derived from the exogenous collagen may be comprised as the exogenous collagen. Those described above can be used as the exogenous collagen and the fragmented collagens.

The concentration of the exogenous collagen in the aqueous medium in the contact step can be appropriately determined depending on the shape and thickness of a three-dimensional tissue of interest (abnormal cardiac rhythm myocardial model), the size of the culture-ware, etc. For example, the concentration of the exogenous collagen in the aqueous medium in the contact step may be 0.1 to 90 wt %, or may be 1 to 30 wt %.

The amount of the exogenous collagen to be used in the contact step may be 0.1 mg or more, may be 0.5 mg or more, 1.0 mg or more, 2.0 mg or more, or 3.0 mg or more, and may be 100 mg or less, or 50 mg or less relative to $1.0 \times 10^5$ to $10.0 \times 10^5$ cells (the number of cells). The exogenous collagen may be added to $2.0 \times 10^5$ to $8.0 \times 10^5$ cells, $3.0 \times 10^5$ to $6.0 \times 10^5$ cells, or $5 \times 10^5$ cells such that the above range is obtained.

The mass ratio (exogenous collagen:cells) between the exogenous collagen and the cells in the contact step is preferably 1000:1 to 1:1, more preferably 900:1 to 9:1, still more preferably 500:1 to 10:1.

If the cardiomyocytes and the collagen-producing cell are used together, the ratio of cardiomyocytes:collagen-producing cell (the number of cells) in the contact step may be 99:1 to 9:1, or may be 80:20 to 50:50.

The method may further comprise a step (precipitation step) of precipitating the fragmented collagens and the cells in the aqueous medium during the contact step or the culturing step. When such a step is carried out, the distribution of the exogenous collagen and the cells in the three-dimensional tissue becomes more uniform. Examples of specific methods include, but should not be limited to, a method of centrifuging a culture solution containing the fragmented collagens and the cells including the cardiomyocytes.

Culturing Step

A process for culturing cells having been brought into contact with the fragmented collagen is not particularly limited. Depending on the types of cultured cells, a suitable culture process may be implemented. For instance, the culture temperature may be from 20° C. to 40° C. or from 30° C. to 37° C. The pH of the culture medium may be from 6 to 8 or from 7.2 to 7.4. The culture period may be from 1 day to 2 weeks, or from 1 week to 2 weeks.

The culture medium is not particularly limited. Depending on the types of cultured cells, a suitable culture medium may be selected. Examples of the culture medium include Eagle's MEM medium, DMEM, Modified Eagle medium (MEM), Minimum Essential medium, RPMI, and GlutaMax medium. The culture medium may be a serum-containing medium or a serum-free medium. The culture medium may be a mixed culture medium prepared by mixing two different culture media.

The cell density in the culture medium in the culturing step can be appropriately determined depending on the shape and the thickness of an abnormal cardiac rhythm myocardial model of interest, the size of the culture-ware, etc. For example, the cell density in the culture medium in the culturing step may be 1 to $10^8$ cells/ml or $10^3$ to $10^7$ cells/ml. In addition, the cell density in the culture medium in the culturing step may be the same as that in the aqueous medium in the contact step.

The three-dimensional tissue has a contraction rate during culturing of preferably 20% or less, more preferably 15% or less, and still more preferably 10% or less. The contraction rate may be calculated by, for instance, the following equation. In the equation, $L_1$ denotes the length of the longest portion of the abnormal cardiac rhythm myocardial model at day 1 of culturing, and $L_3$ denotes the length of the corresponding portion of the three-dimensional tissue at day 3 after culturing.

Contraction rate (%)=$\{(L_1-L_3)/L_1\} \times 100$

Formation Agent for Abnormal Cardiac Rhythm Myocardial Model

A formation agent for an abnormal cardiac rhythm myocardial model according to the present embodiment is a formation agent for an abnormal cardiac rhythm model comprising fragmented collagens, wherein the average length of the fragmented collagens is from 100 nm to 200 µm, and the average diameter of the fragmented collagens is from 50 nm to 30 µm. Regarding the length of the fragmented collagens, the length of 95% of all the fragmented collagens may range from 100 nm to 200 µm. Regarding the diameter of the fragmented collagens, the diameter of 95% of all the fragmented collagens may range from 50 nm to 30 µm.

The "formation agent for an abnormal cardiac rhythm myocardial model" means a reagent for producing an abnormal cardiac rhythm myocardial model. The formation agent for an abnormal cardiac rhythm myocardial model may be in a powder state or in a state of a dispersion in which fragmented collagen has been dispersed in an aqueous medium. Examples of how to prepare fragmented collagen and how to use the formation agent include the processes as indicated above in (Method for Producing Abnormal Cardiac Rhythm Myocardial Model).

Method for Evaluating Drug Efficacy of Heart Disease Therapeutic

As one embodiment of the present invention, a method for evaluating drug efficacy of a heart disease therapeutic using an abnormal cardiac rhythm myocardial model is provided, the method comprising an administration step of administrating a heart disease therapeutic to an abnormal cardiac rhythm myocardial model; and an evaluation step of evaluating drug efficacy from a change in behavior of the cardiac rhythm of the abnormal cardiac rhythm myocardial model to which the heart disease therapeutic is administrated. According to the present embodiment, the drug efficacy of a heart disease therapeutic which affects the cardiac rhythm of the cardiomyocytes can be effectively evaluated.

In the administration step, the heart disease therapeutic is administrated to the abnormal cardiac rhythm myocardial model. Examples of the heart disease therapeutic include cardiac disorder therapeutics such as isoproterenol, myocardial infarction therapeutics such as β blockers and nitrates, and anti-arrhythmia such as amiodarone.

The administration of the heart disease therapeutic may be performed by using a culture medium containing the heart disease therapeutic as a culture medium for culturing the three-dimensional tissue, or may be performed by adding the heart disease therapeutic to a culture medium for culturing the three-dimensional tissue.

The abnormal cardiac rhythm myocardial model to which the heart disease therapeutic is administrated may be composed of a three-dimensional tissue cultured for 1 day or longer, may be composed of a three-dimensional tissue cultured for 5 days or longer, may be composed of a three-dimensional tissue cultured for 6 days or longer, or may be composed of a three-dimensional tissue cultured for days longer than 6 days.

In the evaluation step, the drug efficacy is evaluated from a change in behavior of the cardiac rhythm of the abnormal cardiac rhythm myocardial model to which the heart disease therapeutic is administrated. The drug efficacy can be evaluated using the behavior of the cardiac rhythm as an index. Examples of the behavior of the cardiac rhythm include the beating interval, the number of beats, the force of cardiac rhythm, and the contraction and/or relaxation rate. The change in behavior of the cardiac rhythm may be a change rate of the number of beats and/or a change in beating interval (time between cardiac rhythms) per unit time. The drug efficacy may be evaluated based on the change only in one of these indices, or may be evaluated based on two or more of them.

The evaluation of the drug efficacy can be performed by comparing the behavior of the cardiac rhythm of the abnormal cardiac rhythm myocardial model composed of a three-dimensional tissue to which the heart disease therapeutic is administrated and that of the cardiac rhythm of the abnormal cardiac rhythm myocardial model composed of a three-dimensional tissue to which the heart disease therapeutic is not administrated.

The evaluation step may be performed several times. Namely, the evaluation of the drug efficacy may be performed several times at a predetermined interval after the therapeutic is administrated.

In the evaluation step, the cardiac disorder therapeutic may be evaluated as effective if the number of beats per unit time of the abnormal cardiac rhythm myocardial model to which the heart disease therapeutic is administrated is larger than the number of beats per unit time of the abnormal cardiac rhythm myocardial model to which the heart disease therapeutic is not administrated, and the cardiac disorder therapeutic may be evaluated as not effective if the number of beats per unit time of the abnormal cardiac rhythm myocardial model to which the heart disease therapeutic is administrated is smaller than the number of beats per unit time of the abnormal cardiac rhythm myocardial model to which the heart disease therapeutic is not administrated.

EXAMPLES

Production of Fragmented Collagen (CMF) by Using Type I Collagen

First, lyophilized, pig skin-derived type I collagen manufactured by NH Foods Ltd. was dispersed in 10× phosphate buffered saline (10× PBS), and was subjected to homogenization using a homogenizer for 2 min to prepare fragmented collagen with a diameter of about 20 to 30 µm and a length of about 100 to 200 µm (FIG. 1(A)). The diameter and the length of the fragmented collagen were determined by analyzing individual fragmented collagens by using an electron microscope. The resulting fragmented collagens were washed with a serum-free culture medium (DMEM) to prepare a fragmented collagen culture medium dispersion. The prepared fragmented collagen culture medium dispersion was successfully stored at room temperature for 1 week. The fragmented collagens prepared by the same method as above were used in the production of abnormal cardiac rhythm myocardial models (three-dimensional tissues) described later.

Figure 1B:
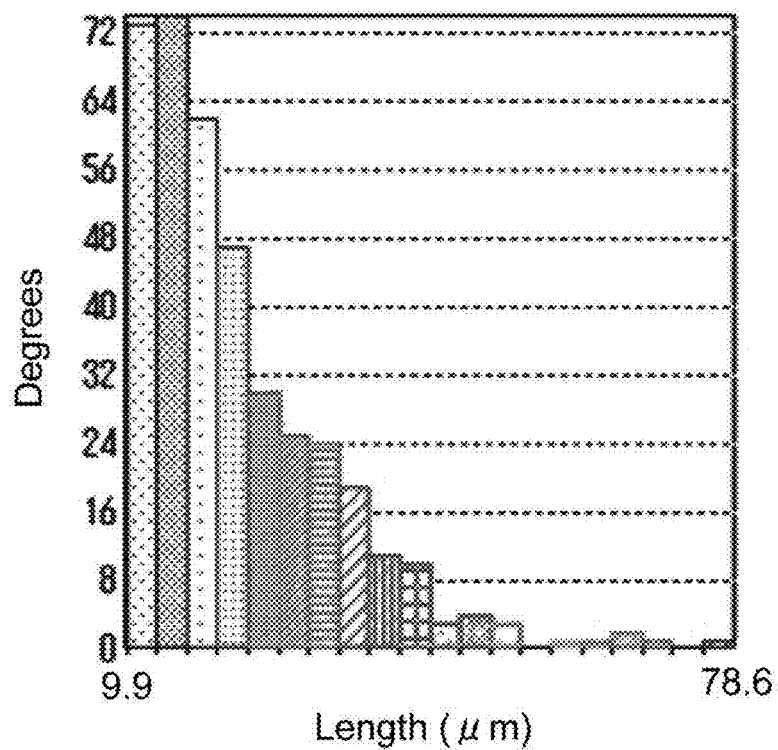
FIG. 1(B) is a histogram showing a length distribution of fragmented collagens obtained by homogenization for 5 min.

In addition, when the homogenization time was changed to 5 min in the above process, fragmented collagen with a diameter of about 950 nm to 16.8 μm and a length of about 9.9 μm to 78.6 μm was obtained (Table 1, FIG. 1(B)). The results have revealed that by adjusting the homogenization time, the size of fragmented collagen can be controlled.

TABLE 1

Size of fragmented collagens after 5-min homogenization (the number of samples: 391)

|  | Length (μm) | Diameter (μm) |
| --- | --- | --- |
| Minimum | 9.9 | 0.95 |
| Maximum | 78.6 | 16.8 |
| Average | 22.5 | 4.4 |
| Standard deviation | 11.0 | 2.6 |

Production of Three-Dimensional Tissue

The fragmented collagens were dispersed with a serum-containing culture medium (DMEM) such that the concentration was 10 mg/ml, thereby preparing a dispersion containing fragmented collagens.

Example 1

Figure 2A:
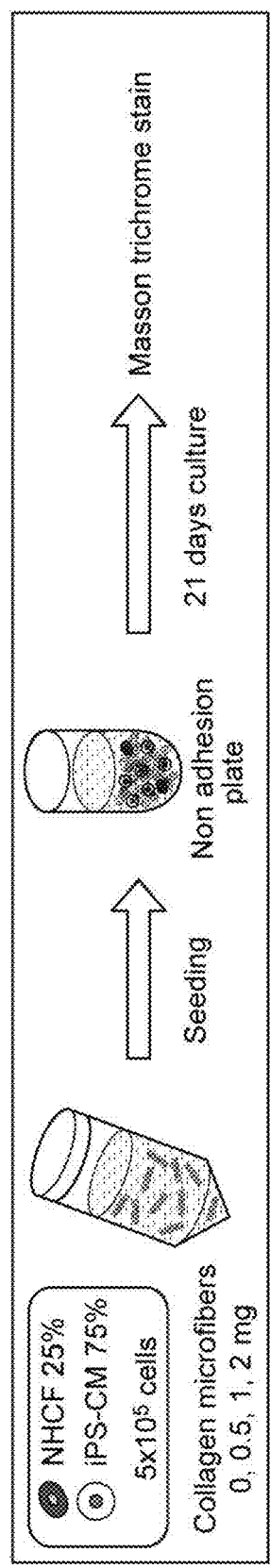
FIGS. 2(A)-2(E) show a schematic view illustrating a production process of a myocardial model (three-dimensional tissue) comprising the fragmented collagens, human cardiac fibroblasts (NHCFs), and iPS cell-derived cardiomyocytes (iPS-CM), and Masson trichrome staining images of the three-dimensional tissues comprising the human cardiac fibroblasts (NHCFs) and the iPS cell-derived cardiomyocytes (iPS-CM).
Figure 2B:
Figure 2D:
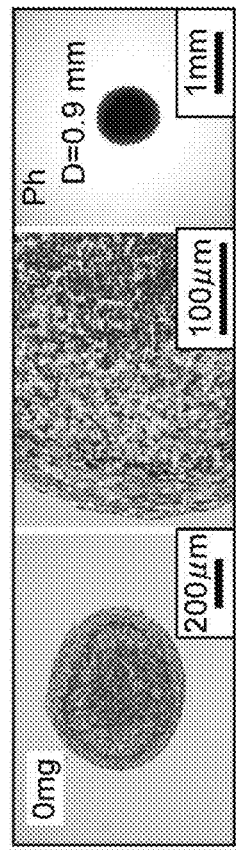
Figure 2C:

A three-dimensional tissue was produced as shown in the schematic view shown in FIG. 2(A). Namely, the dispersion containing the fragmented collagens described above, human cardiac fibroblasts (NHCFs), and human iPS cell-derived cardiomyocytes (iPS-CMs) (hereinafter, NHCFs and iPS-CM are also collectively referred to "cells") were added to a non-adherent 96-well round-bottomed plate to bring the fragmented collagens into contact with the cells (contact step). The dispersion containing the fragmented collagens was added such that the amount of fragmented collagens to be added was 0.5 mg. NHCFs and iPS-CMs were mixed in a proportion of 25:75, and were added such that the total number of cells was $5 \times 10^5$ cells. Subsequently, culturing was performed for a predetermined period (culturing step) to produce three-dimensional tissue 1. Three-dimensional tissue 1 was Masson trichrome stained after 21 days of culturing. An image of three-dimensional tissue 1 taken by using a phase-contrast microscope is shown in FIG. 2(C). Three-dimensional tissue 1 was spherical, and the diameter after 21 days of culturing was about 1.0 mm. In the drawing on the left and that in the center of FIG. 2(C), portions with dark colors indicate collagen fibers and portions with light colors indicate cytoplasm (hereinafter, the same applies to FIGS. 2(B), 2(D), and 2(E)).

Example 2

Three-dimensional tissue 2 was produced in the same manner as in Example 1 except that the dispersion containing the fragmented collagens was added such that the amount of fragmented collagens to be added was 1.0 mg. The results of observation of Masson trichrome stained Three-dimensional tissue 2 by using a phase-contrast microscope are shown in FIG. 2(D). Three-dimensional tissue 2 was spherical, and the diameter after culturing for 21 days was about 1.2 mm.

Example 3

Figure 2E:

Three-dimensional tissue 3 was prepared in the same manner as in Example 1 except that the dispersion containing the fragmented collagens was added such that the amount of fragmented collagens to be added was 1.5 mg. The results of observation of Masson trichrome stained Three-dimensional tissue 3 by using a phase-contrast microscope are shown in FIG. 2(E). Three-dimensional tissue 3 was spherical, and the diameter after culturing for 21 days was about 1.6 mm.

Example 4

Three-dimensional tissue 4 was prepared in the same manner as in Example 1 except that the dispersion containing the fragmented collagens was added except that the amount of fragmented collagens to be added was 3.0 mg. The diameter of three-dimensional tissue 4 after culturing for 7 days was about 4 mm.

Example 5

Three-dimensional tissue 5 was prepared in the same manner as in Example 1 except that the dispersion containing the fragmented collagens was added such that the amount of fragmented collagens to be added was 5.0 mg. The diameter of three-dimensional tissue 5 after culturing for 7 days was about 5 mm.

Comparative Example 1

Comparative three-dimensional tissue 1 was prepared in the same manner as in Example 1 except that the dispersion containing the fragmented collagens was not added. The results of observation of Masson trichrome stained Comparative three-dimensional tissue 1 by using a phase-contrast microscope are shown in FIG. 2(B). Comparative three-dimensional tissue 1 was spherical, and the diameter after culturing for 21 days was about 0.9 mm.

Evaluation

Beating Interval and Force of Cardiac Rhythm of Myocardial Model

Three-dimensional tissues 1 to 5 and Comparative three-dimensional tissue 1 obtained by the above method were used as myocardial models in Examples 1 to 5 and Comparative Example 1, respectively. The beating interval and the force of cardiac rhythm of the myocardial model were evaluated by taking moving images of the cardiac rhythms of the myocardial models after culturing for 7 days by using an inverted microscope, and observing those moving images using image analysis (Image-pro). Specifically, the evaluation was performed based on the moving distance of the center of gravity and the time interval of the cardiac rhythm when the myocardial model beats. FIG. 3 is a diagram illustrating the method for evaluating the beating interval and the force of cardiac rhythm of the myocardial model. The center of gravity of the myocardial model moves according to the cardiac rhythm. The evaluation was performed by measuring the moving distance of the center of gravity when the myocardial model contracts (the distance from the center of gravity shown in FIG. 3(A) to the center of gravity shown in FIG. 3(B)) and the moving distance of the center of gravity when the myocardial model relaxes after contraction (the distance from the center of gravity shown in FIG. 3(B) to the center of gravity shown in FIG. 3(C)). The results are shown in FIGS. 4 to 10.

Figure 4A:
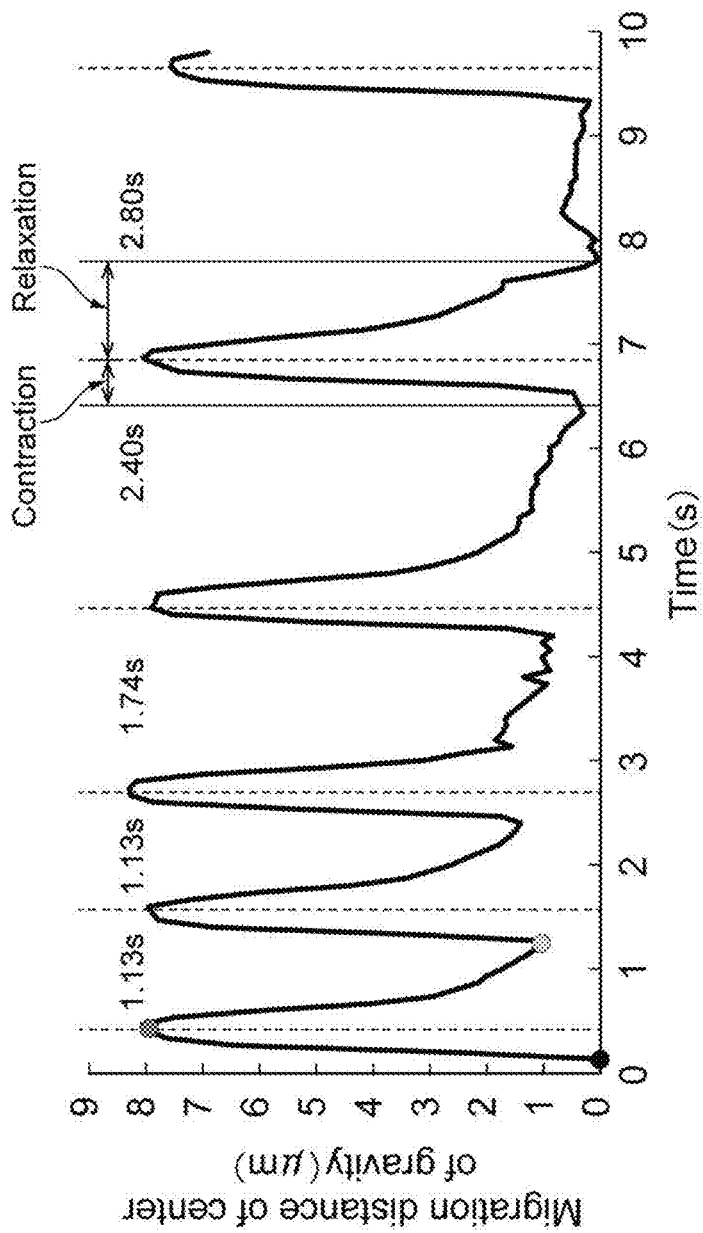
FIGS. 4(A)-4(B) are a graph and images showing the results of evaluation of the cardiac rhythm behavior of a myocardial model.
Figure 4B:
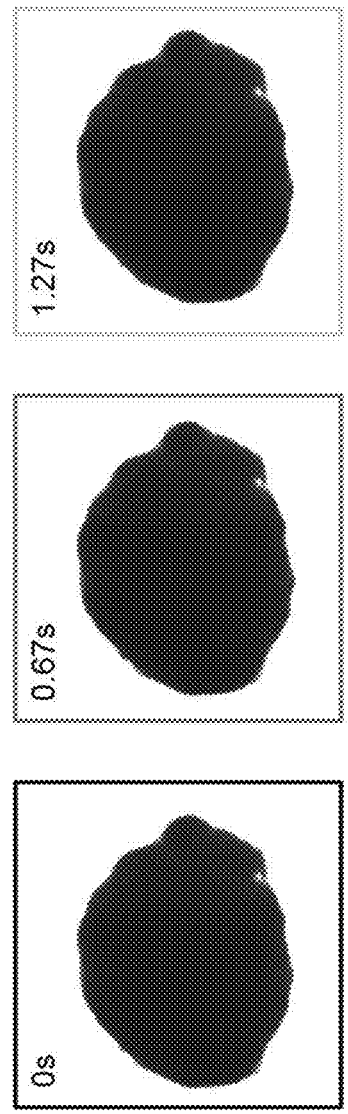

FIG. 4(A) shows the cardiac rhythm behavior of the myocardial model in Example 2, which was obtained by adding 1.0 mg of fragmented collagens. FIG. 4(B) shows the observation start point (0 seconds), a point of contraction (when 0.67 seconds had passed), and a point of relaxation (when 1.27 seconds had passed). FIG. 5(B) shows the cardiac rhythm behaviors of the myocardial models, which were obtained by adding 0 mg, 1.0 mg, and 2.0 mg of fragmented collagens, respectively.

Figure 5A:
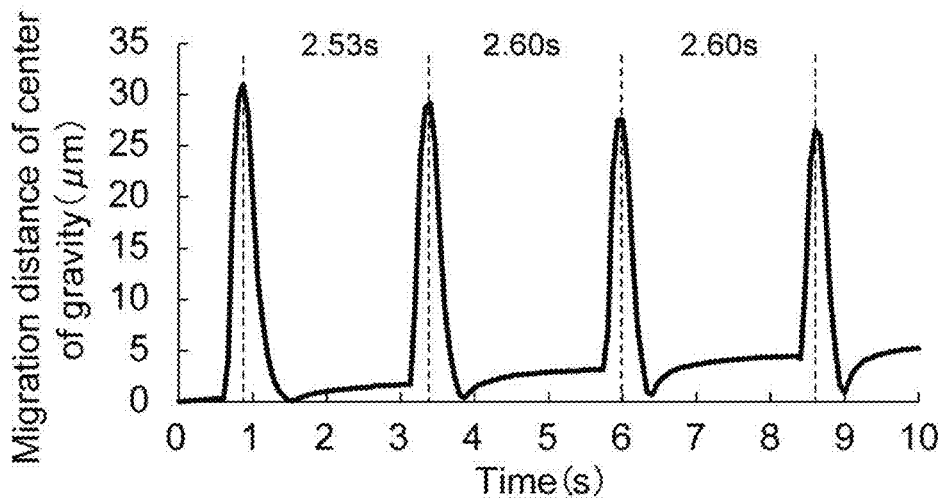
FIGS. 5(A)-5(C) are graphs showing the results of evaluation of the cardiac rhythm behaviors of myocardial models.
Figure 5B:
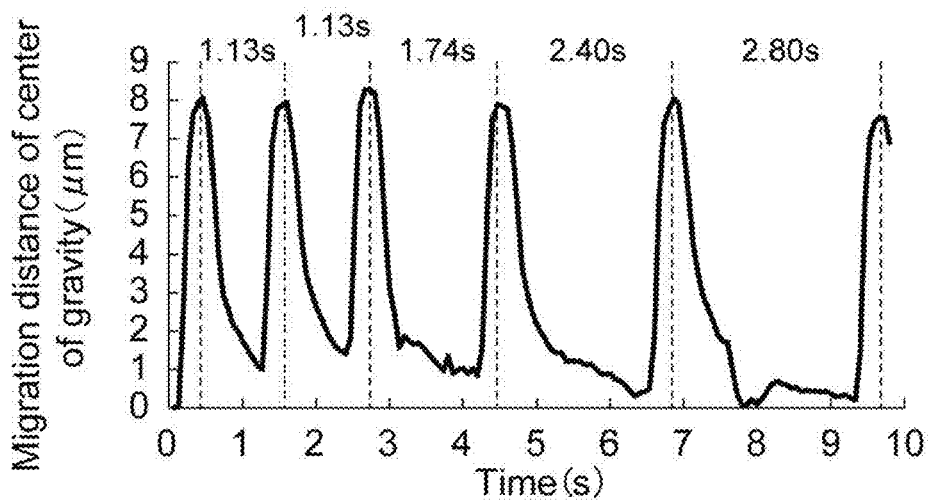
Figure 5C:
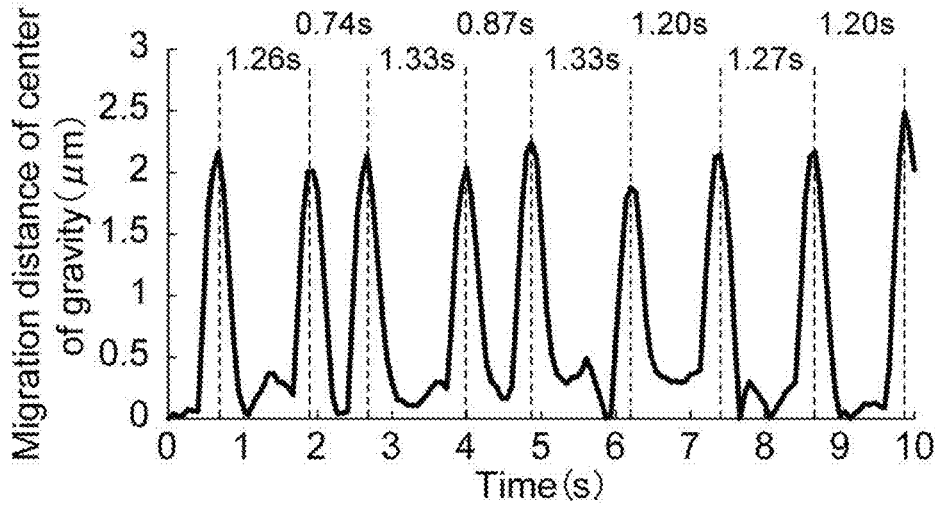

As shown in FIGS. 4 and 5, compared to the case where the fragmented collagens were not added, the cardiac rhythm (the time interval of the cardiac rhythm and the force of cardiac rhythm) of the resulting myocardial model irregularly changed in the case where the fragmented collagens were added. Compared to the case where the collagens were not added, the force of cardiac rhythm of the resulting myocardial model reduced in the case where the collagen was added. As shown in FIG. 5(A), the behavior of the cardiac rhythm was close to the normal one in the myocardial model to which the collagen was not added.

Figure 7A:
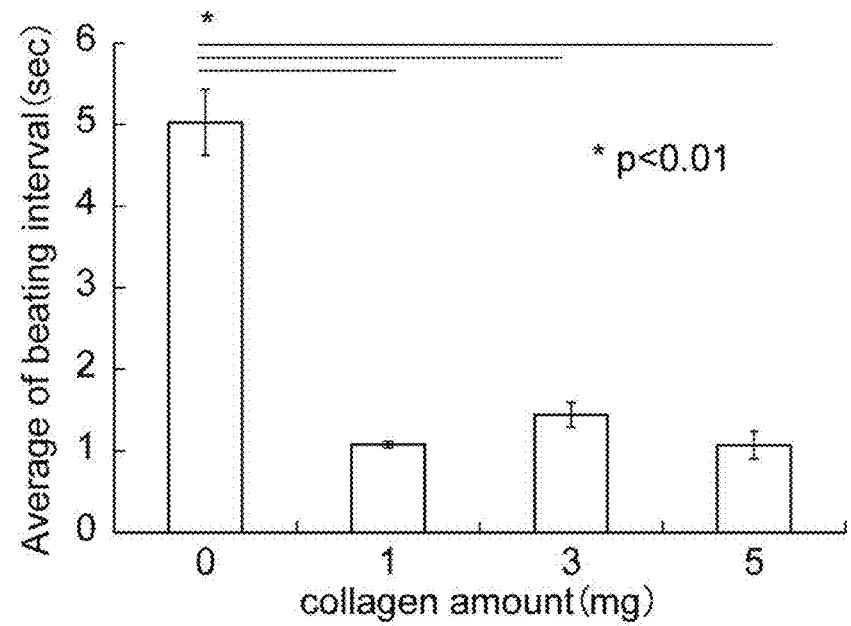
FIGS. 7(A)-7(B) are graphs showing the results of evaluation of the cardiac rhythm behaviors of the myocardial models.
Figure 7B:
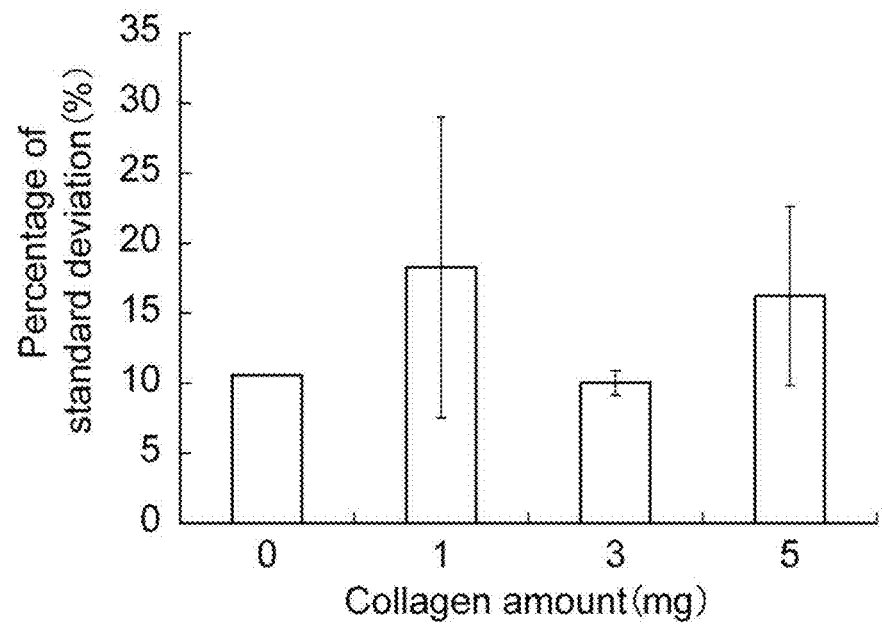
Figure 9:
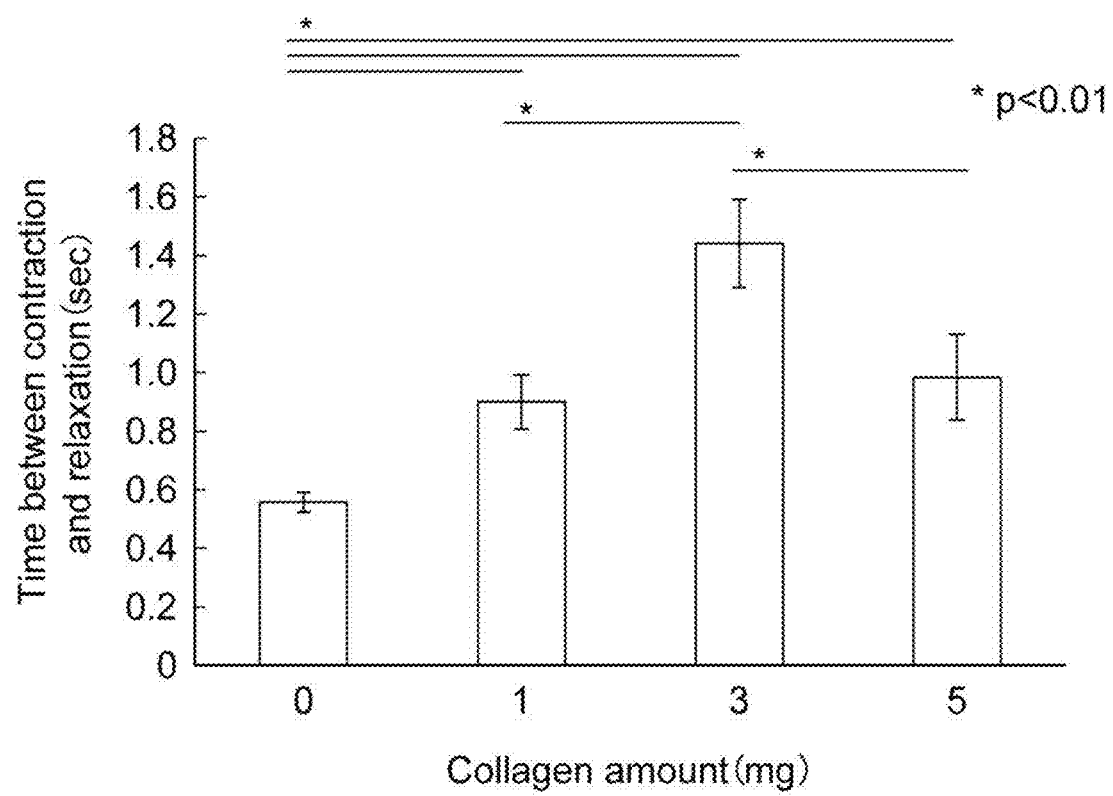
FIG. 9 is a graph showing the results of evaluation of the cardiac rhythm behaviors of the myocardial models.
Figure 10:
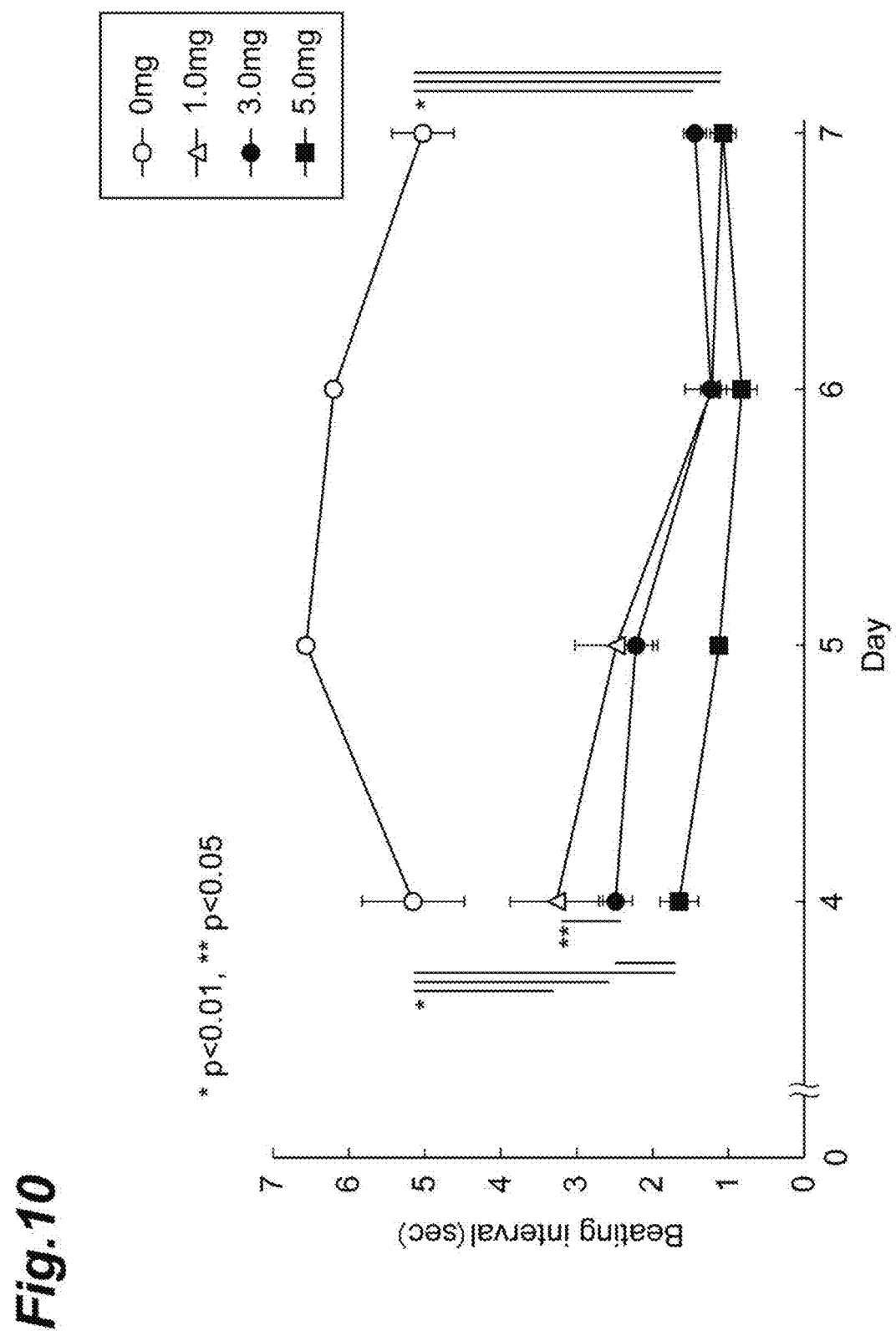
FIG. 10 is a graph showing the results of evaluation of the cardiac rhythm behaviors of the myocardial models.

FIGS. 6(A) to 6(D) and 8(A) to 8(D) show the cardiac rhythm behaviors of the myocardial models where the amounts of fragmented collagens to be used are 0, 1, 3, and 5 mg, respectively. FIG. 7(A) shows an average beating interval (average of beating intervals) calculated from each interval between the dashed lines shown in FIGS. 6 (A) to 6(D) (i.e., the difference between the time when the contraction and relaxation was completed at 1 time and the time when the next contraction and relaxation was completed) (unit: second). FIG. 7(B) shows the average of the standard deviations (S.D.) (an index indicating the irregularity of the cardiac rhythm) from day 4 to day 7 of the culture period. FIG. 9 shows the time (unit: second) between contraction and relaxation of the myocardial model calculated from the intervals indicated by the arrows in FIGS. 8(A) to 8(D) (i.e., the time (unit: second) needed for 1 time of contraction and relaxation). FIG. 10 shows the results of measurement of the beating intervals of the myocardial models according to the number of days of culturing where the amounts of fragmented collagens used were 0 mg, 1 mg, 3 mg, and 5 mg.

As shown in FIG. 7(A), in the myocardial models obtained by adding the fragmented collagens, the average beating intervals were short (namely, the number of beats per unit time was larger). As shown in FIG. 7(B), in the case where 1 mg or 5 mg of fragmented collagen was added, the time interval of the cardiac rhythm more irregularly changed. As shown in FIG. 9, in the myocardial models obtained by adding the fragmented collagens, the time needed for 1 time of contraction and relaxation was longer (namely, the beating rate per 1 time was reduced). As above, it was suggested that the myocardial models produced by adding the fragmented collagens are close to the models where a disease develops. The cardiac rhythm behavior for each collagen amount is shown in FIG. 8. In FIG. 9, the time needed for 1 time of contraction and relaxation was calculated from the results in FIG. 8 to examine the influences by the collagen. As a result, while the time needed for the cardiac rhythm tended to be longer significantly depending on the collagen amount (the amount to be added) at 1 mg and 3 mg, the time needed for the cardiac rhythm at a collagen amount (the amount to be added) of 5 mg was substantially the same as that at 1 mg. It was also suggested that the time of the cardiac rhythm itself can be controlled by the collagen amount. As shown in FIG. 10, the myocardial models obtained by adding the fragmented collagens had a shorter beating interval and a larger number of beats throughout the culture period.

Measurement of Cell Residual Percentage

Construct of Three-Dimensional Tissue 5 mL of 10× phosphate buffered saline (PBS) was added to 50 mg of a pig skin-derived type I collagen (provided by NH Foods Ltd.), and was subjected to homogenization by using a homogenizer for 6 min. Subsequently, centrifugation was performed at 10000 rpm for 3 min to remove the supernatant. 5 mL of serum-free DMEM was added thereto, followed by washing by pipetting for 1 min. After the washing, centrifugation was performed at 10000 rpm for 3 min to remove the supernatant. 5 mL of serum-containing DMEM was added thereto to prepare a culture medium (CMF concentration: 9.8 mg/mL) having fragmented collagens (CMF) dispersed therein. Dispersions were weighed from the culture medium having CMF dispersed therein such that the amounts of CMFs were 0, 1, 2, and 3 mg, were mixed with $5 \times 10^5$ cells of iPS-CM 75%/NHCF 25%, and were seeded in a 96-well round-bottomed non-adherent plate (the amount of the culture medium: 300 μL). Subsequently, centrifugation was performed at 1100 g for 5 min to precipitate the CMFs and the cells. After the centrifugation, culturing was performed in a culture-ware at 37° C. The culture medium was replaced every 2 days by removing the old culture medium and adding 300 μL of new culture medium.

Measurement of DNA Amount

Kit used: DNeasy Blood & Tissue Kit (50) (69504, QIAGEN)

The DNA amount in $5 \times 10^5$ cells of iPS-CM 75%/NHCF 25% was measured using the kit above. The DNA amount at this time was used as a reference (100%). The DNA amounts in the three-dimensional tissues having the CMF amounts after 7 days of the culturing were measured using the kit above. The cell viability (change rate of the DNA amount (change of DNA amount)) in the three-dimensional tissue was calculated using the following equation:

Change rate of DNA amount (%)=(DNA amount in three-dimensional tissue after 7 days of culturing)/(DNA amount in $5 \times 10^5$ cells of iPS-CM 75%/NHCF 25%)×100

The kit above is a commercially available kit containing a DNeasy Mini Spin Column, a collection tube, Buffer ATL, Buffer AL, Buffer AW1, Buffer AW2, Buffer AE, Proteinase K, and the like, and the measurement of DNA was performed according to the following procedure.

A sample to be measured was placed into a 1.5 mL EPPEN tube, and 180 μL of Buffer ATL was added thereto. 20 μL of Proteinase K was added thereto, and was incubated at 56° C. (overnight) until tissues were completely dissolved by performing vortexing. Subsequently, vortexing was performed for 15 seconds, equal amounts of Buffer AL and ethanol were mixed, and 400 μL thereof was added to 1 sample to perform vortexing. The solution was added into a DNeasy Mini Spin Column (hereinafter, simply referred to as a column), and was centrifuged on the condition at 8000 rpm for 1 min. The filtrate and the collection tube were discarded, the column was placed to a new collection tube, and 500 μL of Buffer AW1 was added. Subsequently, centrifugation was performed on the condition at 8000 rpm for 1 min. The filtrate and collection tube were discarded, the column was placed in a new collection tube, and 500 μL of Buffer AW2 was added. After centrifugation on the condition at 14000 rpm for 3 min, the DNeasy membrane was completely dried. The filtrate and the collection tube were discarded, the column was placed in the EPPEN tube (operation 1), 200 µL of Buffer AE was directly added onto the DNeasy membrane (operation 2), and was incubated at room temperature for 1 min (operation 3). Subsequently, centrifugation was performed on the condition at 8000 rpm for 1 min (operation 4). After repeating the operations 1 to 4, the recovered filtrates were combined into an amount of 400 µL. This was measured with Nanodrop.

Figure 11:
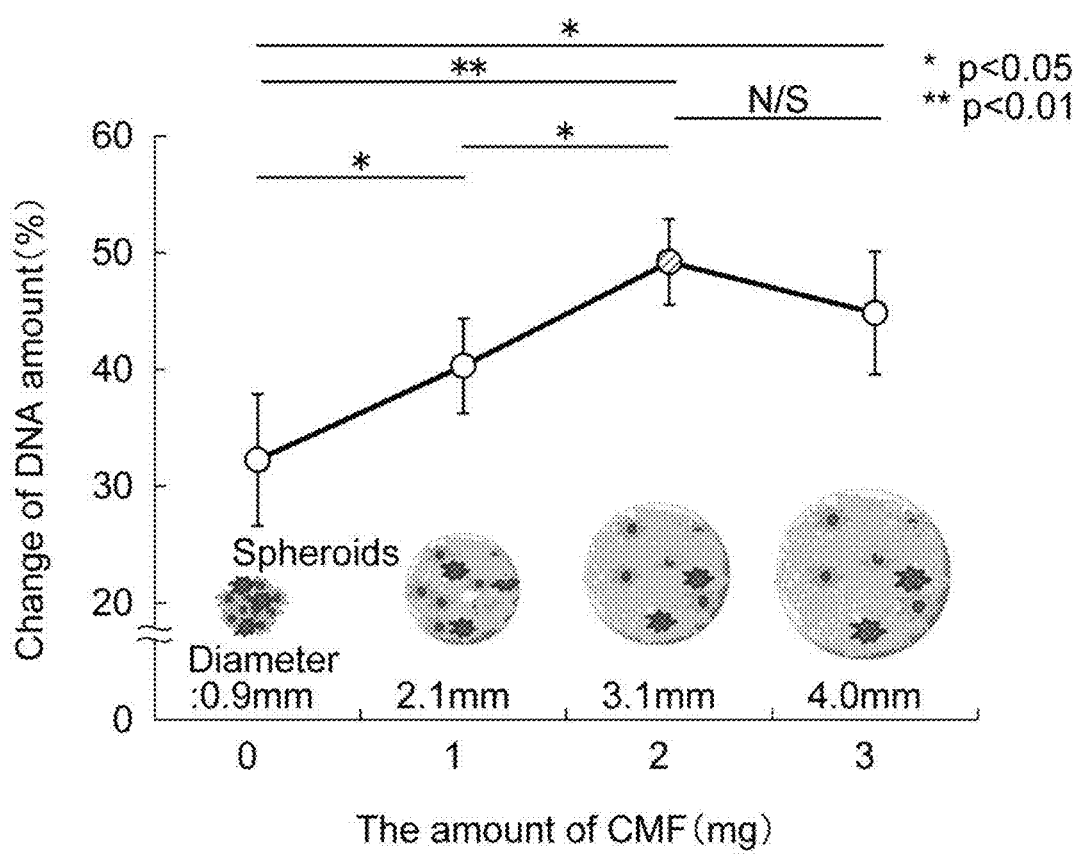
FIG. 11 is a graph showing the results of evaluation of a change in cell viability relative to the amount of the fragmented collagens.

The change rate in DNA amount is shown in FIG. 11. As shown in FIG. 11, as a result of culturing for 7 days, the number of cells in the three-dimensional tissue where CMFs were used increased compared to that of the tissue where the CMFs were not used. It is believed that a larger number of cells survived or the cells survived for a longer time by adding the CMFs and culturing the cells. From the results in FIGS. 10 and 11, the three-dimensional tissue using the CMF after culturing for a long time (at least 7 days) exhibited a cardiac rhythm behavior at a level similar to that at the initial stage of culturing and the cell viability was also higher than the tissue not using the CMFs (spheroids). From this, because a larger number of cells survives or the cells survive for a long time in the myocardial model composed of a three-dimensional tissue using the CMFs, the evaluation of the drug efficacy can be performed over a long time.

Evaluation of Drug Response to Isoproterenol

Construct of Three-Dimensional Tissue

Kit used: Total Collagen Assay Kit (QZBTOTCOL1, QuickZyme Biosciences)

A three-dimensional tissue was constructed in the same manner as above. In a three-dimensional tissue constructed using 1 mg of CMFs, the content of collagen after day 1 of the culturing was 34 wt % based on a lyophilized three-dimensional tissue. The content of the collagen in the three-dimensional tissue was measured using the kit above according to the standard protocol of the kit.

Evaluation of Drug Response

The cardiac rhythms of the tissues after culturing for 5 to 6 days were taken using a SONY Motion analyzer to measure the number of beats. The inside of the microscope was kept at 37° C. during the taking, which was performed for 15 to 20 seconds. After the taking, the plate was extracted once from the microscope to remove the culture medium, and 300 µL of DMEM (tissues to which the drug was not added) or 300 µL of DMEM mixed with 100 nM isoproterenol was added; then, the culture medium was again placed into the microscope, and was incubated at 37° C. After the incubation for 30 min, 60 min, and 80 min, the cardiac rhythms were taken in the same manner as above to measure the number of beats, respectively. From the results of measurement, the change rate of the number of beats (change rate of beating) by adding isoproterenol was calculated from the following equation. For the results, an increase in the number of beats per unit time indicates that the response to isoproterenol was good.

Change rate (%) of the number of beats=(the number of beats at predetermined time in tissues to which drug is added/the number of beats before addition of drug in tissues to which drug is added)/(the number of beats at predetermined time in tissues to which drug is not added/the number of beats before replacement of culture medium in tissues to which drug is not added)×100

The change rate of the number of beats caused by addition of isoproterenol is determined by the equation above, and this value is corrected by the equation below, i.e., by dividing this value by the change rate of the number of beats when the drug is not added (=a change in the number of beats caused by replacement of the culture medium).

Figure 12:
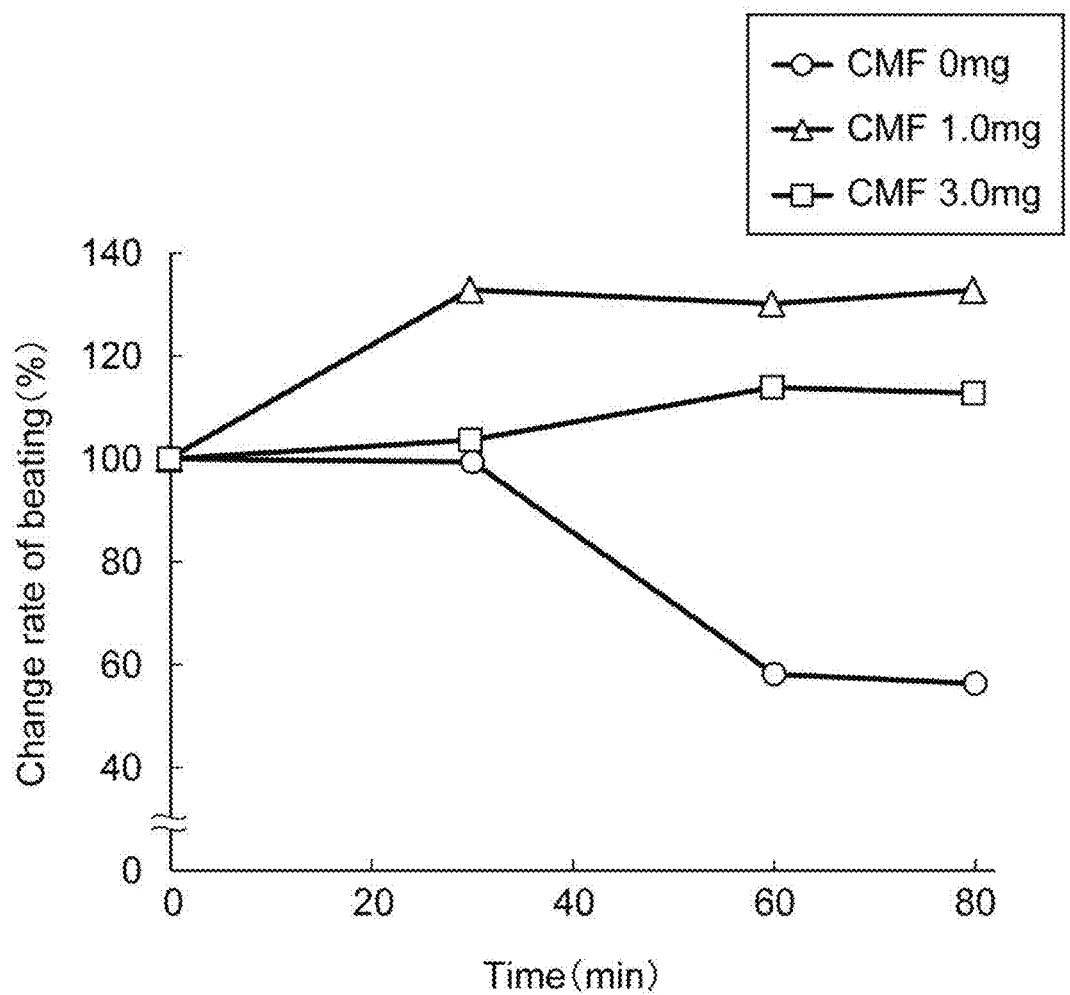
FIG. 12 is a graph showing the results of evaluation of a change rate of the number of beats of the myocardial model after isoproterenol is added.

FIG. 12 shows the results of the change rate of the number of beats. In the myocardial models, the drug response was poor in the case where the amount of CMFs used was 0 mg, and the drug response was exhibited in the case where the amount of CMFs used were 1 mg and 3 mg. The myocardial model where the amount of CMFs used was 1 mg exhibited more favorable drug response.

The results of evaluation of the drug efficacy using the myocardial models composed of the three-dimensional tissues using the CMFs are consistent with the knowledge of the effect of isoproterenol acting on the adrenergic receptor of cardiac muscles to enhance the contraction force, and it is shown that the effect of the cardiac disorder therapeutic can be correctly evaluated by the myocardial model composed of the three-dimensional tissue using the CMFs.

INDUSTRIAL APPLICABILITY

According to the present invention, a novel abnormal cardiac rhythm myocardial model can be provided, and its applications to development of an effective drug for diseases attributed to the abnormal cardiac rhythm of the heart and the like are expected.

The invention claimed is:

1. A method for evaluating drug efficacy of a heart disease therapeutic, comprising:
    an administration step comprising administering the heart disease therapeutic to an abnormal cardiac rhythm myocardial model composed of a three-dimensional tissue comprising cells, wherein said cells comprise cardiomycetes and collagen, wherein said collagen comprises fragmented collagen having an average length from 100 nm to 200 µm with a triple helix structure, and said collagen is present in an amount of 0.1 mg or more relative to $1.0 \times 10^5$ to $10.0 \times 10^5$ of the cells, and wherein the abnormal cardiac rhythm myocardial model having a beating interval that changes irregularly, wherein at least a portion of the cells adheres to the collagen; and
    an evaluation step comprising evaluating the drug efficacy by a change in behavior of a cardiac rhythm of the abnormal cardiac rhythm myocardial model to which the heart disease therapeutic is administered.

2. The method for evaluating drug efficacy of a heart disease therapeutic according to claim 1,
    wherein in the evaluation step, the heart disease therapeutic is evaluated as effective as a cardiac disorder therapeutic if a number of beats per unit time of the abnormal cardiac rhythm myocardial model to which the heart disease therapeutic is administrated is larger than that of the abnormal cardiac rhythm myocardial model to which the heart disease therapeutic is not administrated, and
    the heart disease therapeutic is evaluated as not effective as the cardiac disorder therapeutic if the number of beats per unit time of the abnormal cardiac rhythm myocardial model to which the heart disease therapeutic is administrated is smaller than that of the abnormal cardiac rhythm myocardial model to which the heart disease therapeutic is not administrated.

3. The method for evaluating drug efficacy of a heart disease therapeutic according to claim 1, wherein the evaluation step is performed several times.

4. The method for evaluating drug efficacy of a heart disease therapeutic according to claim 1,
wherein the collagen comprise fragmented fibrillar collagen.

5. The method for evaluating drug efficacy of a heart disease therapeutic according to claim 1, wherein the average length of the fragmented collagen is from 22 μm to 200 μm.

6. The method for evaluating drug efficacy of a heart disease therapeutic according to claim 1, wherein the average length of the fragmented collagen is from 100 μm to 200 μm.

7. The method for evaluating drug efficacy of a heart disease therapeutic according to claim 1, wherein an average diameter of the fragmented collagen is 50 nm to 30 μm.

8. The method for evaluating drug efficacy of a heart disease therapeutic according to claim 1, wherein an average diameter of the fragmented collagen is 4μm to 30 μm.

9. The method for evaluating drug efficacy of a heart disease therapeutic according to claim 1, wherein an average diameter of the fragmented collagen is 20 μm to 30 μm.

10. The method for evaluating drug efficacy of a heart disease therapeutic according to claim 1, wherein the average length of the fragmented collagen is from 22 μm to 200 μm, and an average diameter of the fragmented collagen is 50 nm to 30 μm.

11. The method for evaluating drug efficacy of a heart disease therapeutic according to claim 1, wherein a content of the cardiomyocytes is 5 to 95% by mass based on the three-dimensional tissue.

12. The method for evaluating drug efficacy of a heart disease therapeutic according to claim 1, wherein a content of the cardiomyocytes is 25% to 75% by mass based on the three-dimensional tissue.

13. The method for evaluating drug efficacy of a heart disease therapeutic according to claim 1, wherein the cells further contain a collagen-producing cell.

14. The method for evaluating drug efficacy of a heart disease therapeutic according to claim 1, wherein the cells further contain fibroblasts.

15. The method for evaluating drug efficacy of a heart disease therapeutic according to claim 1, wherein a content of the collagen is from 10 to 90 wt % based on the three-dimensional tissue.

16. The method for evaluating drug efficacy of a heart disease therapeutic according to claim 1, wherein a content of the collagen is from 10 to 40 wt % based on the three-dimensional tissue.

17. A method for evaluating drug efficacy of a heart disease therapeutic, comprising:
a contact step comprising bringing cells comprising cardiomycetes into contact with exogenous collagen in an aqueous medium;
a culturing step of culturing the cells in contact with the exogenous collagen to obtain an abnormal cardiac rhythm myocardial model composed of a three-dimensional tissue containing cells comprising cardiomycetes and collagen, wherein the abnormal cardiac rhythm myocardial model having a beating interval that changes irregularly, and wherein at least a portion of the cells adheres to the collagen;
an administration step of administering the heart disease therapeutic to the abnormal cardiac rhythm myocardial model; and
an evaluation step of evaluating the drug efficacy by a change in behavior of a cardiac rhythm of the abnormal cardiac rhythm myocardial model to which the heart disease therapeutic is administered,
wherein an amount of the exogenous collagen is 0.1 mg or more relative to $1.0 \times 10^5$ to $10.0 \times 10^5$ of the cells, and wherein the collagen comprises fragmented collagen comprising an average length from 100 nm to 200 μm, and the fragmented collagen has a triple helix structure.

18. The method according to claim 17, further comprising a step of precipitating the exogenous collagen and the cells in the aqueous medium during the contact step or the culturing step.

19. The method according to claim 17, wherein a mass ratio between the exogenous collagen and the cells in the contact step is 900:1 to 9:1.

20. The method for evaluating drug efficacy of a heart disease therapeutic according to claim 17, wherein the cells further contain collagen-producing cells, and a ratio of cardiomyocytes: collagen-producing cells (a number of the collagen-producing cells) in the contact step is 99:1 to 9:1.

* * * * *

UNITED STATES PATENT AND TRADEMARK OFFICE
CERTIFICATE OF CORRECTION

PATENT NO. : 12,326,433 B2
APPLICATION NO. : 16/644059
DATED : June 10, 2025
INVENTOR(S) : Michiya Matsusaki et al.

Page 1 of 1

It is certified that error appears in the above-identified patent and that said Letters Patent is hereby corrected as shown below:

On the Title Page

Column 2, Line 6:
Item (56) Delete "cardiomycetes" and insert -- cardiomyocytes --.

In the Claims

Column 16, Line 38:
In Claim 1, delete "cardiomycetes" and insert -- cardiomyocytes --.

Column 18, Line 11-12:
In Claim 17, delete "cardiomycetes" and insert -- cardiomyocytes --.

Column 18, Line 16:
In Claim 17, delete "cardiomycetes" and insert -- cardiomyocytes --.

Signed and Sealed this
Eleventh Day of November, 2025

John A. Squires
*Director of the United States Patent and Trademark Office*